US007637877B2

(12) United States Patent
Hofmann et al.

(10) Patent No.: US 7,637,877 B2
(45) Date of Patent: Dec. 29, 2009

(54) ULTRASONIC SHOCK WAVE HEAD FOR USE IN LITHOTRIPSY

(75) Inventors: Kirsten Hofmann, Igelheim (DE); Herbert Tauber, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 856 days.

(21) Appl. No.: 10/549,281

(22) PCT Filed: Mar. 22, 2004

(86) PCT No.: PCT/EP2004/003020

§ 371 (c)(1), (2), (4) Date: Sep. 13, 2005

(87) PCT Pub. No.: WO2004/093056

PCT Pub. Date: Oct. 28, 2004

(65) Prior Publication Data

US 2006/0189870 A1 Aug. 24, 2006

(30) Foreign Application Priority Data

Apr. 16, 2003 (DE) ................................ 103 17 541

(51) Int. Cl.
*A61N 7/00* (2006.01)

(52) U.S. Cl. ........................................................... 601/2

(58) Field of Classification Search ................. 600/459; 601/2–4; 606/128
See application file for complete search history.

(56) References Cited

U.S. PATENT DOCUMENTS

| | | | | |
|---|---|---|---|---|
| 3,387,604 | A | 6/1968 | Erikson | |
| 4,928,672 | A | 5/1990 | Grasser et al. | |
| 5,222,483 | A | 6/1993 | Plisek | |
| 5,279,282 | A | 1/1994 | Oppelt | |
| 7,189,209 | B1 * | 3/2007 | Ogden et al. | 601/2 |

FOREIGN PATENT DOCUMENTS

| | | |
|---|---|---|
| DE | 37 39 390 | 6/1989 |
| FR | 2 669 248 A1 | 11/1990 |
| FR | 2 669 248 | 5/1992 |
| WO | WO 95/24159 | 9/1995 |

* cited by examiner

*Primary Examiner*—Eric F Winakur
*Assistant Examiner*—Michael T Rozanski
(74) *Attorney, Agent, or Firm*—Schiff Hardin LLP

(57) ABSTRACT

Disclosed is an ultrasonic shock wave head for use in lithotripsy, comprising a shock wave source (2) and an acoustic lens (6) for focusing the ultrasonic shock wave generated by the shock wave source (2). A bearing housing (8) for the shock wave source (2) is molded onto said acoustic lens (6) as a single piece.

7 Claims, 1 Drawing Sheet

ULTRASONIC SHOCK WAVE HEAD FOR USE IN LITHOTRIPSY

BACKGROUND OF THE INVENTION

1. Field of the Invention

The present invention relates to an ultrasonic shock wave head for lithotripsy.

2. Description of the Prior Art

An ultrasonic shock wave head for lithotripsy (as is known, for example, from WO 95/24159 or DE 37 39 390 A1) has a number of individual components that are arranged in a housing. The individual components, in particular the lens used for focusing of the ultrasonic shock waves and the actual shock wave source (i.e. the transducer generating the ultrasound), must be spatially positioned exactly relative to one another in the housing of the ultrasonic shock wave head in order to ensure a reproducible position of the focus. This is connected with a significant production-related effort.

SUMMARY OF THE INVENTION

An object of the present invention is now based on the object to provide a ultrasonic shock wave head for lithotripsy that is simple to produce and in which a high reproducibility of the position of the focus is ensured.

The above object is achieved in accordance with the present invention by an ultrasonic shock wave head for lithotripsy, having a shock wave source and an acoustic lens for focusing the ultrasonic shock wave generated by the shock wave source, wherein the lens has a support housing for the shock wave source integrally molded with the lens as one piece.

Since a support housing for the shock wave source is integrally molded as one piece on the acoustic lens, a high reproducibility of the relative positioning of the acoustic lens and shock wave source is ensured with a simultaneously simpler, cost-saving manufacture. The lens and the support housing for the shock wave source thus form an integral component that can be produced in a single fabrication operation, for example using an injection molding type method.

DESCRIPTION OF THE DRAWINGS

The single figure is a side sectional view of an ultrasonic shock wave head constructed in accordance the present invention.

DESCRIPTION OF THE PREFERRED EMBODIMENTS

Figure 1:
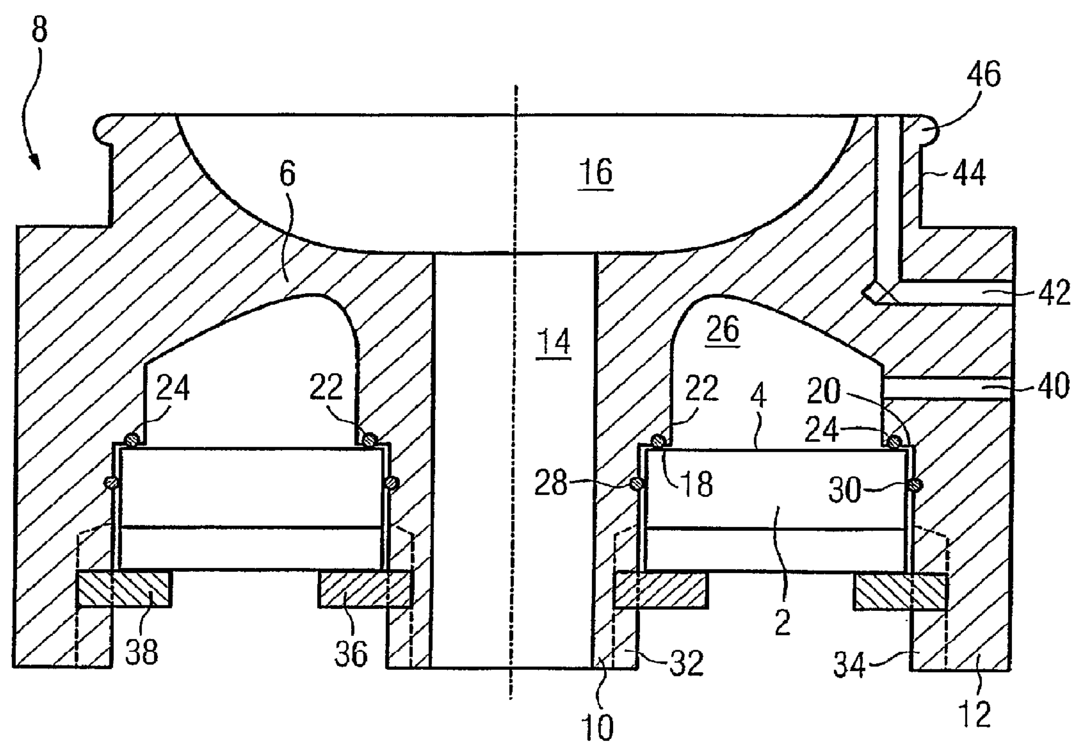

According to the invention, an ultrasonic shock wave head has an annular (with respect to the indicated dot-and-dash center axis) shock wave source 2 with planar radiation surface 4. An acoustic lens 6 is arranged at a distance from this radiation surface 4, the acoustic lens 6 being biconvex in the exemplary embodiment and focusing the ultrasonic shock waves emitted by the shock wave source 2 in a focus (not shown in the figure).

A support housing 8 for accommodation of the shock wave source 2 is integrally molded as one piece with the acoustic lens 6. This support housing 8 has an inner, approximately hollow-cylindrical wall part 10 that is concentrically surrounded by an outer wall part 12 (likewise integrally-molded with the lens 6). The hollow space 14 surrounded by the inner wall part 10 extends up to the acoustic lens 6 and empties into the coupling space 16 bounded thereby, the coupling space 16 being filled with a coupling fluid (normally water) in operation of the device. The hollow space 14 serves for acquisition of an image-generating ultrasonic transducer arrangement that generates an A-image or a B-image and serves for monitoring of the correct positioning of the focus in the body of a patient.

Annularly circumferential shoulders or sections 18 and 20 are integrally molded on the outer surface of the inner wall part 10 and the inner surface of the outer wall pear 12, on which shoulders or segments 18 and 20 the shock wave source 2 rests on the edge of its radiating surface 4, respectively over an interleaving sealing rings 22 and 24. An approximately annular chamber 26 located between the shock wave source 2 and the acoustic lens 6 and filled with fluid in operation is sealed fluid-tight by this sealing ring 22, 24. In the exemplary embodiment, further sealing rings 28, 30 are optionally provided at the sealing rings 22, 24 in order to seal the chamber 26.

The inner wall part 10 is provided with an external threading 32 on its outer circumference and the outer wall part is provided with an inner threading 34 into which are screwed compression rings 36 and 38 with which the shock wave source 2 is pressed against the sections 18, 20 and is fixed in this position.

The support housing 8 and additionally has fluid-conducting channels 40, 42 that interconnect with the chamber 26 and the coupling space 16 before the acoustic lens 6 and serve for filling the chamber 26 and the coupling space 16 with the coupling fluid. The support housing 8 is provided in the region of the acoustic lens 6 on its outer circumference with an annular, circumferential recess 44 that serves for fluid-tight application of an elastic coupling membrane.

The acoustic lens 6 and the support housing 8 form a one-piece, integral component that is comprises of a polymer material and can be produced in an injection-molding method in a single fabrication step. Since the support housing 8 formed in this manner for the shock wave source 2 simultaneously forms the acoustic lens 6 or conversely the acoustic lens 6 is simultaneously the support housing 8 for the shock wave source 2, it is ensured that, without additional adjustment measures, lens 6 and shock wave source 2 are always positioned correctly both with regard to separation (spacing) and with regard to the axial alignment (center position and angle setting of the axis).

Although modifications and changes may be suggested by those skilled in the art, it is the intention of the inventors to embody within the patent warranted heron all changes and modifications as reasonably and properly come within the scope of their contribution to the art.

The invention claimed is:

1. An ultrasonic shock wave head for lithotripsy, comprising:

a shock wave source that emits an ultrasonic shock wave;

a unitary, one-piece molded element;

said molded element comprising a lens configuration therein forming an acoustic lens disposed in a path of said ultrasonic shock wave having a shape that focuses said ultrasonic shock wave; and said molded element comprising a support housing configuration therein, integrally molded as one piece with said lens configuration, said support housing configuration having a shape that holds said shock wave source in said molded element, and said shock wave source being retained in said molded element by said support housing configuration.

2. An ultrasonic shock wave head as claimed in claim 1, wherein said shock wave source has an annular shape and wherein said support housing configuration comprises walls integrally molded therein forming an annulus, said shock wave source being disposed and held in said annulus.

3. An ultrasonic shock wave head as claimed in claim 1, comprising a chamber molded into said support housing configuration between said shock wave source and said lens configuration.

4. An ultrasonic shock wave head as claimed in claim 3, comprising a channel molded into said support housing configuration communicating said chamber with an exterior of said molded element, and being configured to convey fluid from the exterior of said molded element into said chamber.

5. An ultrasonic shock wave head as claimed in claim 1, wherein said support housing configuration comprises a coupling space molded therein, disposed in said support housing configuration following said lens configuration in a direction of propagation of said ultrasonic shock wave.

6. An ultrasonic shock wave head as claimed in claim 5, comprising a channel molded into said support housing configuration and communicating said coupling space with an exterior of said molded element, said channel being adapted to convey fluid from said exterior of said molded element into said coupling space.

7. An ultrasonic shock wave head as claimed in claim 1, wherein said support housing has an exit face at which said ultrasonic shock waves exit from said support housing configuration and wherein said support housing configuration comprises an annular recess laterally surrounding said exit face and being adapted for fluid-type application of a coupling membrane thereto.

* * * * *